US012661455B2

(12) United States Patent
Andreasson

(10) Patent No.:  US 12,661,455 B2
(45) Date of Patent:      Jun. 23, 2026

(54) DISPOSABLE NEEDLE-HOLDING CARTRIDGE FOR A DEVICE FOR COSMETIC TREATMENTS

(71) Applicant: CAMPOMATS S.R.L., Riccione (IT)

(72) Inventor: Mats Andreasson, Riccione (IT)

(73) Assignee: CAMPMATS S.R.L., Riccione (IT)

( * ) Notice: Subject to any disclaimer, the term of this patent is extended or adjusted under 35 U.S.C. 154(b) by 521 days.

(21) Appl. No.: 18/263,486

(22) PCT Filed: Dec. 29, 2021

(86) PCT No.: PCT/IB2021/062429
§ 371 (c)(1),
(2) Date: Jul. 28, 2023

(87) PCT Pub. No.: WO2022/172082
PCT Pub. Date: Aug. 18, 2022

(65) Prior Publication Data
US 2024/0082503 A1      Mar. 14, 2024

(30) Foreign Application Priority Data

Feb. 11, 2021     (IT) ........................ 102021000003065

(51) Int. Cl.
*A61M 5/32*        (2006.01)
*A61M 37/00*       (2006.01)
(52) U.S. Cl.
CPC ...... *A61M 5/3202* (2013.01); *A61M 37/0076* (2013.01)

(58) Field of Classification Search
CPC ........................ A61M 5/3202; A61M 37/0076
(Continued)

(56) References Cited

U.S. PATENT DOCUMENTS 9,629,991 B1 *   4/2017   O'Brien, III ............. A61N 1/40
9,636,491 B1     5/2017   O'Brien, III et al.
(Continued)

FOREIGN PATENT DOCUMENTS

CN          2356645 Y      1/2000
CN          106902452 A    6/2017
(Continued)

*Primary Examiner* — Phillip A Gray
(74) *Attorney, Agent, or Firm* — Laubscher & Fretwell, P.C.

(57)                ABSTRACT
A needle-holding cartridge for cosmetic treatments includes a casing with a first part, intended to be rested on a zone of the body of a patient in which a cosmetic treatment has to be performed, and a second part intended to be inserted into and locked in an appropriate seat obtained at an end of a device for cosmetic treatments, inside the first part of the casing a support element being arranged that can slide inside the casing; to the support element a single needle or a plurality of needles is fixed that can protrude from the casing through an opening placed at a first end of the casing, the support element being provided with a rod-shaped appendage, a portion of which protrudes from the casing through a hole obtained at a second end of the casing, opposite the first end; the needle-holding cartridge further includes a first ring-shaped sealing element that surrounds the appendage and is inserted into a seat obtained at the second end of the casing, and a sheath-shaped second sealing element placed on said portion of the appendage.

8 Claims, 3 Drawing Sheets

(58) Field of Classification Search
    USPC ......................................................... 604/192
    See application file for complete search history.

(56) References Cited

U.S. PATENT DOCUMENTS

| | | | | |
|---|---|---|---|---|
| 2008/0009802 | A1* | 1/2008 | Lambino | A61M 37/0015 |
| | | | | 604/173 |
| 2014/0094742 | A1* | 4/2014 | Won | A61M 37/0076 |
| | | | | 604/46 |
| 2015/0151098 | A1* | 6/2015 | Spendlove | A61M 37/00 |
| | | | | 606/186 |

FOREIGN PATENT DOCUMENTS

| | | | |
|---|---|---|---|
| IT | 102019000015560 | | 9/2019 |
| KR | 20170123756 | A | 11/2017 |
| WO | 2020166760 | A1 | 8/2020 |

* cited by examiner

DISPOSABLE NEEDLE-HOLDING CARTRIDGE FOR A DEVICE FOR COSMETIC TREATMENTS

BACKGROUND OF THE INVENTION

The invention relates to a needle-holding cartridge, in particular a disposable needle-holding cartridge usable with devices for cosmetic treatments, in particular devices for so-called PMU (permanent make-up) devices, i.e. treatments for making tattoos or semipermanent make-up, like, for example making tattooed eyebrows, lips and contours, eyeliner, or tattooed areolas of nipples for women who have undergone a mastectomy, and micro-needling or micro-pricking treatments intended, for example, to smooth wrinkles, remove scars or improve skin tone in a treatment zone, stimulating the production of collagen.

Needle-holding cartridges are known that include a casing, inside which a needle-holding unit is arranged consisting of a support element to which a single needle or a plurality of needles can be fixed.

The needle-holding unit can slide inside the casing of the cartridge so that the ends of the needles can protrude from the cartridge and from the body of the device. Sliding the needle-holding unit being controlled by a drive device fitted inside the body of a so-called device and driven by an electric motor.

The type of needles to be used depends on the type of treatment to be applied. For example, for making tattoos or a semipermanent make-up, a cartridge with a single needle or with a group of three or five needles is used, whereas for micro-needling or micro-pricking treatments, cartridges with a high number of needles are used, even up to several dozen together.

Also the penetration depth of the needle, or of the needles, in the skin depends on the treatment to be applied and can vary from a few tenths of a millimetre to a few millimetres, for example from 0.15 mm to 2.5 mm.

One problem connected to the use of the needle-holding cartridges is that of preventing body fluids of the patient, or liquid substance injected into the skin of the patient during treatment possibly flowing back through the cartridge, leaking outside the cartridge and contaminating the device that uses the cartridge.

Needle-holding cartridges are known from the prior art inside which needle-holding units are slidable, including a needle-holding support to which a single needle or a plurality of needles can be fixed. The needle-holding support can slide inside the cartridge and can be driven with alternating motion by a drive motor that acts on a rod-shaped appendage of the needle-holding support.

In order to prevent a flow back to the exterior of the cartridge of body fluids or of liquid substances injected during permanent make-up, micro-needling or micro-pricking treatments, one or two absorbent elements or barriers can be provided inside the cartridge, which are used to absorb said body fluids and said liquid substances. These absorbing elements are in the form of drilled disks arranged around the aforesaid rod-shaped appendage. The absorbing elements are not however able to act as seals and cannot prevent a certain quantity of body fluids or of liquid substances leaking therebetween and the rod-shaped appendage, thus being able to reach outside the cartridge.

Cartridges of this type are disclosed, for example, in U.S. Pat. Nos. 9,629,991 and 9,636,491.

Arranging a ring seal between the rod-shaped appendage and the bottom wall of the cartridge in a hole is known through which the rod-shaped appendage traverses an end of which protrudes outside the cartridge.

This seal is not however able to completely prevent leaking outside the cartridge of liquid substances or of body fluids, mainly owing to the alternating motion of the rod-shaped appendage that deforms repeatedly the ring seal, compromising the seal function thereof.

SUMMARY OF THE INVENTION

One object of the present invention is to provide a needle-holding cartridge, in particular a disposable needle-holding cartridge, usable in a device for cosmetic treatments, such as permanent make-up treatments, micro-needling or micro-prickling treatments, and other treatments defined as nano treatments, said cartridge having to ensure that body fluids or liquid substances injected during these treatments can flow outside the cartridge, contaminating the device that uses the cartridge and making the device no longer usable without being subjected to complex and costly sterilization treatments.

The object of the invention is reached with a needle-holding cartridge for cosmetic treatments according to claim 1.

Owing to the invention, it is possible to prevent with certainty the leak outside the cartridge, in particular towards the device that uses the cartridge, of body fluids or liquid substances injected during treatments performed with the help of the cartridge.

Further features and advantages of the invention are clear from the description which follows, with reference to the appended drawings, in which:

DETAILED DESCRIPTION

Figures 1, 2:
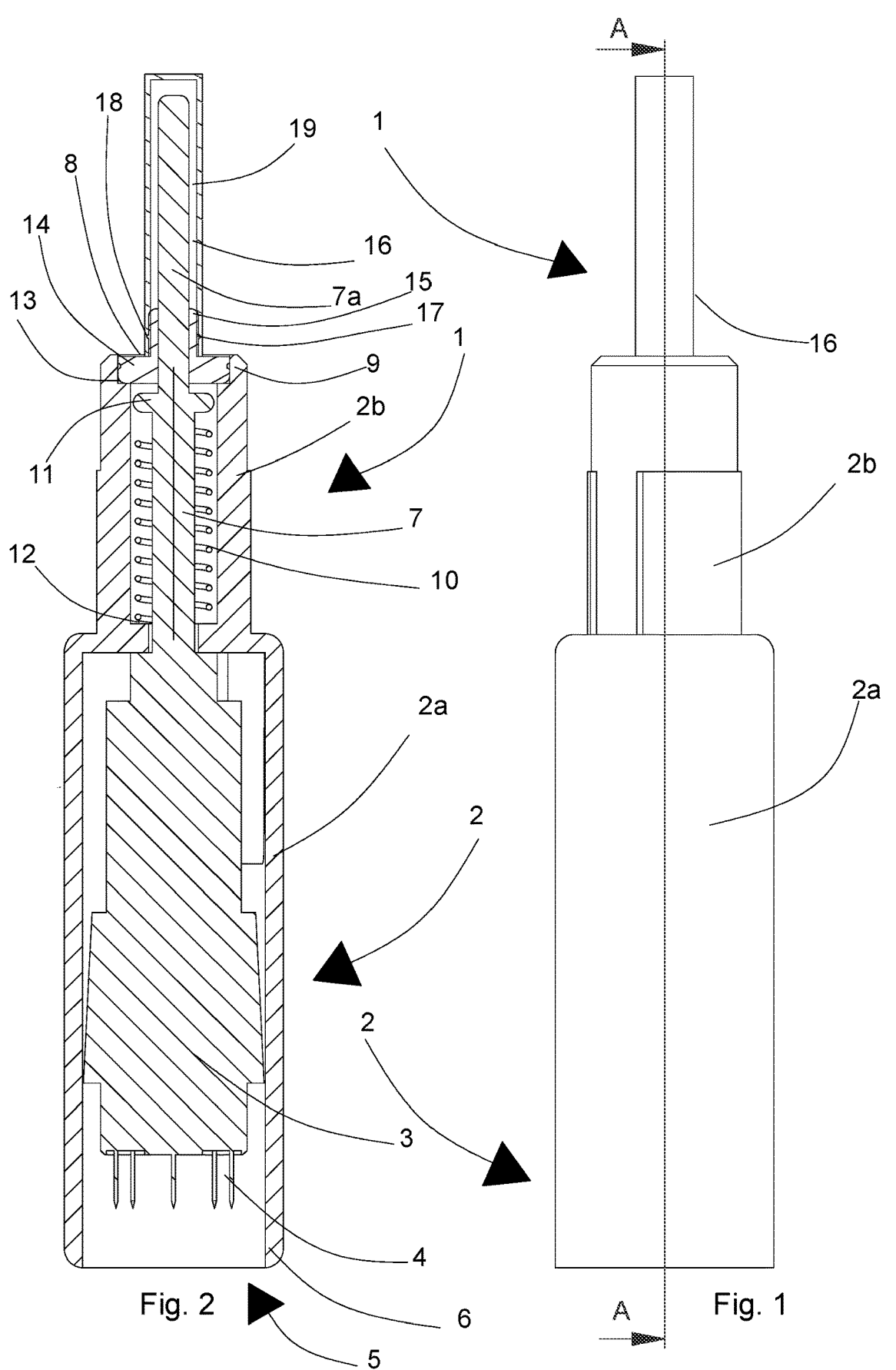
FIG. 1 is an elevation view of a first embodiment of a needle-holding cartridge according to the invention.
FIG. 2 is a section of the cartridge of FIG. 1, along line A-A in FIG. 1.
Figures 5, 6:
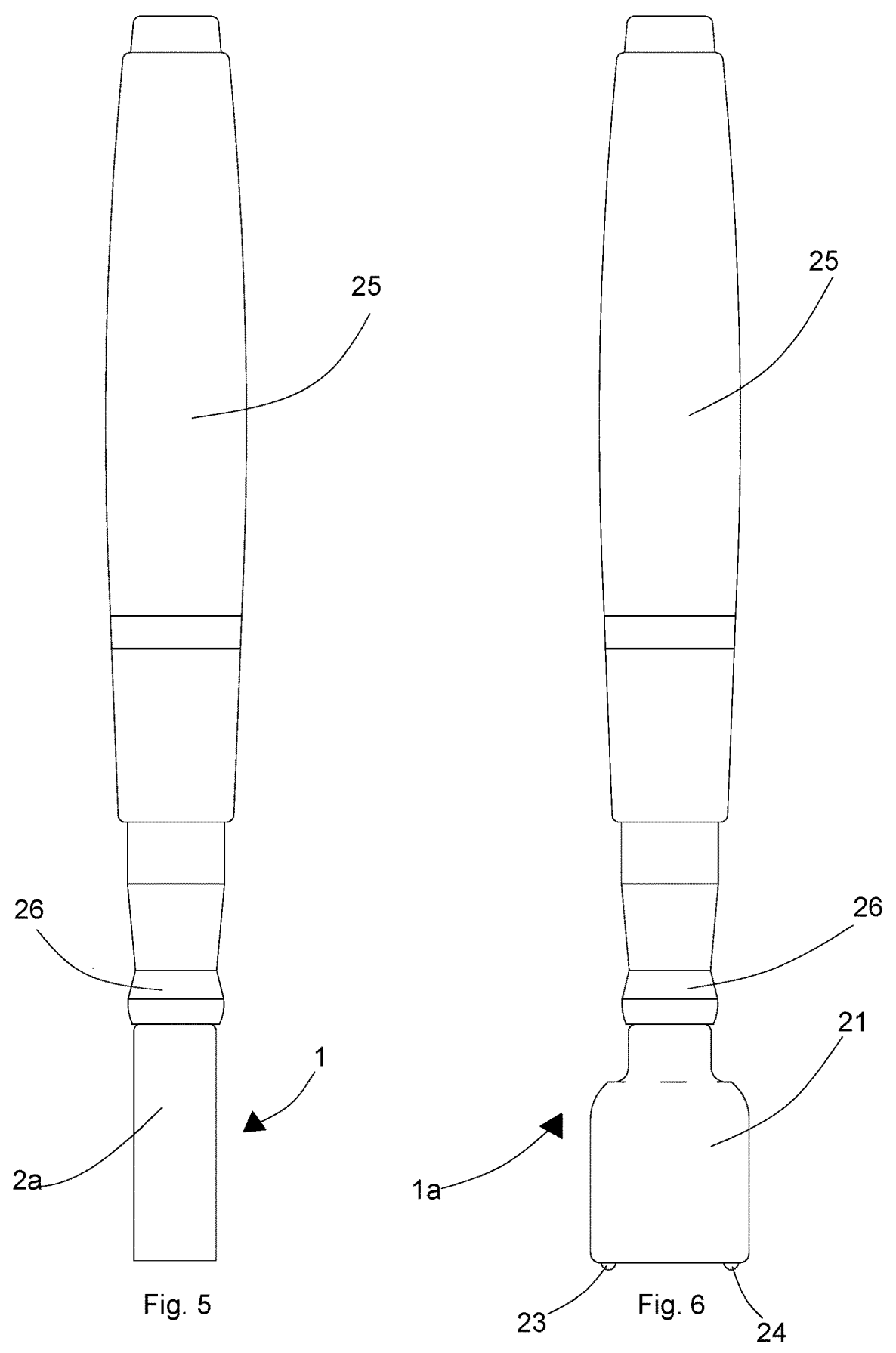
FIG. 5 shows a cartridge like the one illustrated in FIGS. 1 and 2, fitted to a device for cosmetic treatments.
FIG. 6 shows a cartridge like the one illustrated in FIGS. 3 and 4, fitted to a device for cosmetic treatments.

In FIGS. 1 and 2 a first embodiment is illustrated of a needle-holding cartridge 1 according to the invention, which is usable with a device 25 for cosmetic treatments, a so-called "device", for example of the type disclosed in patent application 102019000015560, filed in the name of the applicant of this application. In FIG. 5, a needle-holding cartridge 1 is illustrated that is inserted into the aforesaid device 25.

The needle-holding cartridge 1 includes a casing 2, which can be transparent or semitransparent or also opaque.

The casing 2 includes a first part 2a, intended to be rested on a zone of the body of a patient in which a cosmetic treatment has to be performed, and a second part 2b intended to be inserted and locked in an appropriate seat obtained in an end 26 of the device 25.

Inside the first part 2a of the casing 2, a support element 3 is arranged that can slide axially inside the casing 2. To the support element 3, a plurality of needles 4 is fixed that can protrude from the casing 2 through an opening 5 placed at a first end 6 of the casing 2. The support element 3 is made so as to determine the maximum protrusion of the needles 4 from the opening 5, said protrusion being able to vary from about 0.3 mm to about 2.5 mm, depending on the type of treatment to be performed.

The support element 3 is provided with a rod-shaped appendage 7 that protrudes from the casing 2 through a hole 8 placed at a second end 9 of the casing 2, opposite the first end 6.

When the cartridge 1 is inserted into the device 25, the appendage 7 interacts with a driving arrangement provided in the device 25 that exerts a thrust on the appendage 7, so as to move the support element 3 from an initial position shown in FIG. 1 in which the needles 4 are retracted inside the casing 2 to a final position (not illustrated in the Figures) in which the needles 4 protrude from the opening 5, by a preset protrusion.

On the rod-shaped appendage 7, a coil spring 10 is positioned, arranged between a collar 11 that is part of the appendage 7 and a resting surface 12 obtained in the casing 2.

The coil spring 10 is used to return the support element 3 to the initial position thereof when the thrust of the driving arrangement on the appendage 7 ceases, so as to be able to perform an alternating movement of the support element 3.

At the end 9 of the casing 2, a seat 13 is obtained, into which a first ring-shaped sealing element 14 that surrounds the appendage 7 is inserted. The first ring-shaped sealing element 14 is provided with a cylindrical protuberance 15 that also surrounds the appendage 7 and protrudes outside the cartridge 1 through the hole 8. The first ring-shaped sealing element 14 hinders a leak of body fluids or liquids in general through the hole 8 of the cartridge 1.

On a portion 7a of the appendage 7, which protrudes outside the cartridge 1 through the hole 8a, a sheath-shaped second sealing element 16 is placed, fitted to the cylindrical protuberance 15 of the first ring-shaped sealing element 14. The second ring-shaped sealing element 16 can be, for example, made of silicone. The cylindrical protuberance 15 is provided with a radial annular protrusion 17, shaped so as to be inserted into a corresponding groove 18 of the second ring-shaped sealing element 16, to lock the second ring-shaped sealing element 16 in position on the cylindrical protuberance 15.

Between the second sealing element 16 and the portion 7a of the appendage 7, a closed space 19 is defined that is used to trap possible fractions of body fluids or liquids in general that may leak between the first sealing element 14 and the appendage 7, preventing the possible body fluids or liquids from being able to exit into the space outside the cartridge 1.

The combined action of the first sealing element 14 and of the second sealing element 16 ensures that not even the smallest quantity of body fluids or liquids in general can exit the cartridge 1 during use thereof and contaminate the device 25 on which the cartridge 1 is installed.

Figures 3, 4:
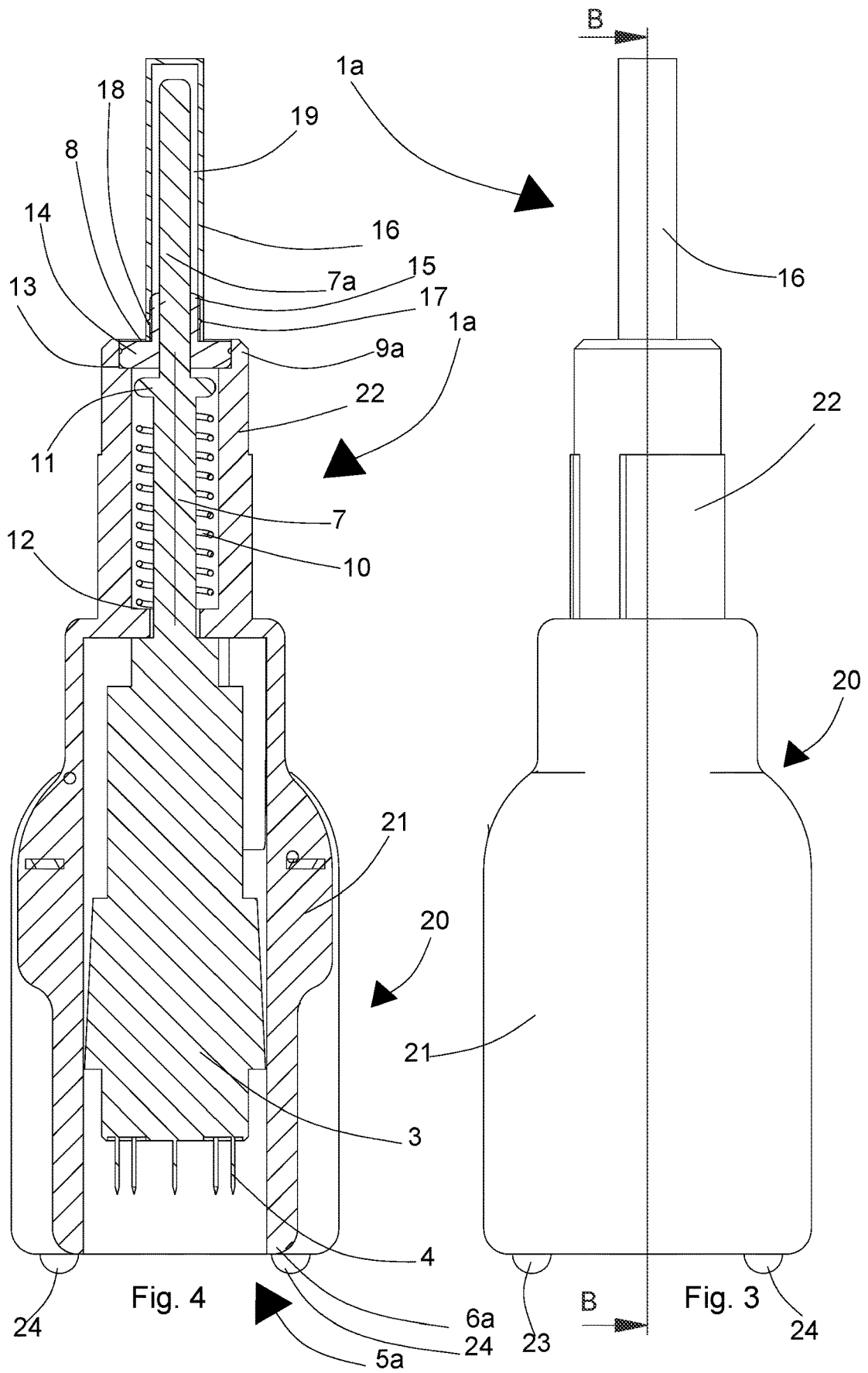
FIG. 3 is an elevation view of a second embodiment of a needle-holding cartridge according to the invention.
FIG. 4 is a section of the cartridge of FIG. 3, along line B-B in FIG. 3.

In FIGS. 3 and 4, a second embodiment of a needle-holding cartridge 1a according to the invention is illustrated, which is usable with a device 25 for cosmetic treatments, a so-called "device", for example of the type disclosed in patent application 102019000015560, filed in the name of the applicant of this application.

In FIG. 6, a needle-holding cartridge 1a is illustrated that is inserted into the aforesaid device 25.

Parts of the needle-holding cartridge 1a that are substantially identical to parts of the needle-holding cartridge 1, which was disclosed previously, are marked by the same reference numbers used for the needle-holding cartridge 1, illustrated in FIGS. 1 and 2.

The needle-holding cartridge 1a includes a casing 20, which can be transparent or semitransparent or also opaque.

The casing 20 includes a first part 21, intended to be rested on a zone of the body of a patient in which a cosmetic treatment has to be performed, and a second part 22, substantially identical to the second part 2a of the casing 2 of the cartridge 1, intended to be inserted and locked in an appropriate seat obtained in an end 26 of the device 25.

Inside the first part 21 of the casing 20, a support element 3 is arranged that can slide axially inside the casing 2. To the support element 3, a plurality of needles 4 is fixed that can protrude from the casing 20 through an opening 5a placed at a first end 6a of the casing 20. The support element 3 is made so as to determine the maximum protrusion of the needles 4 from the hole 5a, said protrusion being able to vary from about 0.3 mm to about 2.5 mm, depending on the type of treatment to be performed.

The support element 3 is provided with a rod-shaped appendage 7, which protrudes from the casing 2 through a hole 8 placed at a second end 9a of the casing 2, opposite the first end 6a.

When the cartridge 1a is inserted into the device 25, the appendage 7 interacts with a driving arrangement provided in the device 25 that exerts a thrust on the appendage 7, so as to move the support element 3 from an initial position shown in FIG. 3 in which the needles 4 are retracted inside the casing 20, to a final position (not illustrated in the figures) in which the needles 4 protrude from the opening 5a, by a set protrusion.

On the rod-shaped appendage 7, a coil spring 10 is positioned, arranged between a collar 11 that is part of the appendage 7 and a resting surface 12 obtained in the casing 20.

The coil spring 10 is used to return the support element 3 to the initial position thereof when the thrust of the driving arrangement on the appendage 7 ceases, so as to be able to perform an alternating movement of the support element 3.

At the end 9a of the casing 20, a seat 13 is obtained into which a first ring-shaped sealing element 14 is inserted that surrounds the appendage 7. The first ring-shaped sealing element 14 is provided with a cylindrical protuberance 15 that also surrounds the appendage 7 and protrudes outside the cartridge 1 through the hole 8. The first sealing element 14 is used to hinder an exit of body fluids or liquids in general through the hole 8 of the cartridge 1.

On a portion 7a of the appendage 7 which protrudes outside the cartridge 1a through the hole 8, a sheath-shaped second sealing element 16 is placed that is fitted to the cylindrical protuberance 15 of the first sealing element 14. The second sealing element 16, can be, for example, made of silicone. The cylindrical protuberance 15 is provided with a radial annular protrusion 17, shaped so as to be inserted into a corresponding groove 18 of the second sealing element 16, to lock the second sealing element 16 in position on the cylindrical protuberance 15.

Between the second sealing element 16 and the portion 7a of the appendage 7, a closed space 19 is defined that is used to trap possible fractions of body fluids or liquids in general that may leak between the first sealing element 14 and the appendage 7, hindering the body fluids or liquids from being able to leak into the space outside the cartridge 1.

The combined action of the first sealing element 14 and of the second sealing element 16 ensures that not even the smallest quantity of body fluids or liquids in general can exit the cartridge 1*a* during use thereof and contaminate the device 25 on which the cartridge 1*a* is installed.

In the first part 21 of the casing 20 a first pair of electrodes 23 and a second pair of electrodes 24 are inserted that protrude from the first end 6*a* of said first part 21, as can be seen in FIGS. 3 and 4.

The electrodes 23 and 23 are used to apply a radio frequency alternating current to the skin of a patient during a cosmetic treatment. The radio frequency alternating current can be applied both simultaneously to the treatment with the needles 4, and independently of the treatment with needles 4.

The electrodes 23 and 24 can be supplied for example by the device 25.

The object of the application of the radio frequency current is to obtain a lifting effect due to the action of the current on the proteins of the collagen, with consequent relaxing of the skin.

The invention claimed is:

1. Needle-holding cartridge for cosmetic treatments including a casing, which includes a first part, intended to be rested on a zone of the body of a patient in which a cosmetic treatment has to be performed, and a second part intended to be inserted and locked in an appropriate seat obtained in an end of a device for cosmetic treatments, wherein inside the first part of the casing a support element is arranged, which can slide inside the casing; wherein onto the support element a plurality of needles is fixed that can protrude from the casing through an opening placed at a first end of the casing, wherein the support element is provided with a rod-shaped appendage, a portion of which protrudes from the casing through a hole obtained at a second end of the casing, opposite the first end, wherein it further includes a first ring-shaped sealing element that surrounds the appendage and is inserted into a seat obtained at said second end of the casing, wherein a sheath-shaped second sealing element is placed on said portion of the appendage.

2. Needle-holding cartridge according to claim 1, wherein the first sealing element is provided with a cylindrical protuberance that also surrounds the appendage and protrudes outside the cartridge-through the hole obtained at the second end of the casing.

3. Needle-holding cartridge according to claim 2, wherein the second sheath-shaped sealing element is fitted to the cylindrical protuberance of the first sealing element.

4. Needle-holding cartridge according to claim 2, wherein the cylindrical protuberance of the first sealing element is provided with a radial annular protrusion, shaped to be inserted into a corresponding groove of the second sealing element.

5. Needle-holding cartridge according to claim 1, wherein between the second sealing element and the portion of the appendage a closed space is defined.

6. Needle-holding cartridge according to claim 1, wherein the second sealing element is made of silicone.

7. Needle-holding cartridge according to claim 1, wherein on the rod-shaped appendage a coil spring is positioned that is arranged between a collar that is part of the appendage and a resting surface obtained in the casing.

8. Needle-holding cartridge according to claim 1, wherein a first pair of electrodes and a second pair of electrodes, that protrude from the first end of the first part are inserted into said first part of the casing.

* * * * *